United States Patent
Cane'

(10) Patent No.: US 10,842,930 B2
(45) Date of Patent: Nov. 24, 2020

(54) DEVICE FOR INFUSING A FLUID SUBSTANCE TO THE BODY OF A LIVING BEING

(71) Applicant: Cane' S.p.A., Rivoli (IT)

(72) Inventor: Mario Cane', Collegno (IT)

(73) Assignee: Cane' S.p.A., Rivoli (IT)

( * ) Notice: Subject to any disclaimer, the term of this patent is extended or adjusted under 35 U.S.C. 154(b) by 0 days.

(21) Appl. No.: 14/817,788

(22) Filed: Aug. 4, 2015

(65) Prior Publication Data
US 2017/0035963 A1 Feb. 9, 2017

(51) Int. Cl.
*A61M 5/158* (2006.01)

(52) U.S. Cl.
CPC ..... *A61M 5/158* (2013.01); *A61M 2005/1581* (2013.01); *A61M 2005/1587* (2013.01)

(58) Field of Classification Search
CPC .............. A61M 5/14248; A61M 5/158; A61M 2005/1581; A61M 5/14; A61M 5/00; A61M 5/14244; A61M 5/142; A61M 2005/14253; A61M 2005/1587; A61M 2005/14256; A61M 2005/1426; A61M 2005/14264; A61M 2005/14268; A61M 2005/14272; A61M 2005/1586; A61M 2005/3022
See application file for complete search history.

(56) References Cited

U.S. PATENT DOCUMENTS

| | | | |
|---|---|---|---|
| 4,662,872 A | 5/1987 | Cane' | |
| 4,813,939 A | 3/1989 | Marcus | |
| 5,716,343 A * | 2/1998 | Kriesel | A61M 5/1409 128/DIG. 12 |
| 5,858,005 A * | 1/1999 | Kriesel | A61M 5/14248 128/DIG. 26 |
| 6,447,487 B1 | 9/2002 | Cane' | |
| D565,176 S | 3/2008 | Cane' | |
| 7,407,493 B2 | 8/2008 | Cane' | |
| D659,234 S | 5/2012 | Cane' | |
| 8,172,814 B2 | 5/2012 | Cane' | |
| 2003/0149405 A1* | 8/2003 | Enns | A61M 5/158 604/273 |
| 2007/0016129 A1* | 1/2007 | Liniger | A61M 5/158 604/93.01 |
| 2008/0312601 A1 | 12/2008 | Cane | |

(Continued)

FOREIGN PATENT DOCUMENTS

TW M277463 U 10/2005

OTHER PUBLICATIONS

Italian Search Report and Written Opinion issued in connection with co-pending Italian Patent Application TO2014A000086 filed on Feb. 4, 2014.

(Continued)

*Primary Examiner* — Kevin C Sirmons
*Assistant Examiner* — Alexandra Lalonde
(74) *Attorney, Agent, or Firm* — Howson & Howson LLP (57) ABSTRACT

Device (11) for infusing a fluid substance into the body of a living being, comprising a hollow duct body (13) in which a rectilinear distal portion (15), a middle portion (17) and a proximal portion (19) are defined, wherein the distal portion (15) terminates with a pointed end (21) and extends along an axis substantially perpendicular to a plane in which the middle portion (17) extends, characterized in that the middle portion (17) comprises a curved section (23).

3 Claims, 6 Drawing Sheets

(56) References Cited

U.S. PATENT DOCUMENTS

| | | | |
|---|---|---|---|
| 2010/0063453 A1* | 3/2010 | Theander | A61M 5/158 604/180 |
| 2010/0100050 A1 | 4/2010 | Cane | |
| 2011/0172608 A1 | 7/2011 | Cane' | |
| 2012/0143133 A1 | 6/2012 | Cane' | |
| 2014/0361048 A1 | 12/2014 | Cane' | |
| 2015/0038906 A1 | 2/2015 | Cane' | |

OTHER PUBLICATIONS

European Search Report and Written Opinion issued in connection with co-pending European Patent Application No. 15153543 Date filed on: Jul. 21, 2015.

* cited by examiner

DEVICE FOR INFUSING A FLUID SUBSTANCE TO THE BODY OF A LIVING BEING

BACKGROUND

The invention relates to a device for infusing a fluid substance into the body of a living being. The invention notably relates to the field of infusion of medical substances in liquid form into the body of a living being.

The invention finds application particularly in all those cases in which a fluid substance is to be administered in a subcutaneous way to a patient's body.

Devices for infusing a fluid substance, especially liquid medicinal substances, into the body of a living being are known. Such known devices are made as hollow needles provided with a pointed end. Such needles are usually made of stainless steel. In the case of subcutaneous infusions, for instance, needles are known that are called butterfly needles because they have a pair of lateral tabs made of plastics, which facilitate gripping and fixing to the patient's body. In particular, among the butterfly-type needles there are also known needles comprising two rectilinear portions either perpendicular to each other or arranged along oblique axes forming an angle with each other that is usually approximately 90°. Such needle is described for instance in TWM277463(U). Infusion needles bent at 90° are particularly advantageous for prolonged subcutaneous infusions, owing to the fact that they reduce space requirement and patient discomfort. Indeed, after a first distal portion of the needle has been inserted into the skin for infusion, the second proximal portion, which receives the drug from a cannula attached to the needle, is parallel to the skin surface and adhering thereto.

Needles with 90° bent end, however, have the drawback that they are brittle. The 90° bending determines indeed a zone susceptible to breaking. This zone is notoriously brittle because of the working operations required for obtaining the bent shape. Furthermore the needle body is extremely rigid and it is not generally capable of absorbing repeated stresses that tend to modify the bending angle. When the 90° bent needle has been introduced into the patient's skin, the proximal portion that remains outside is fixed to the patient's body, for instance by means of a plaster, for preventing the needle from moving. However, between the needle distal portion inserted into the skin and the proximal portion remaining outside forces are generated that tend to vary the bending angle between the two portions. These forces are caused by movements of the patient's skin, said movements being either voluntary, for example in a patient undergoing a therapy during his usual everyday activities, or involuntary, as is the case with skin movements provoked by respiration or by body movements during sleep. These forces act in two opposite directions, because they tend both to enlarge the bending angle and to reduce it, and they are often repetitive and act in rapid succession. The bending zone of the needle is therefore subjected to a remarkable stress and it is not unusual that breaking occurs. This drawback has been found especially in the case of prolonged therapies, i.e. therapies that last at least eight hours or longer. Therapies of such duration are known for example in the case of Parkinson's disease and thalassemia. In the event of breaking, the needle distal portion is usually retained inside the patient's skin and often tends to penetrate deeply, as it is no longer connected to the proximal outer portion.

The breaking of needles with 90° bent end constitutes a remarkable inconvenience and cases of patients that retain several tens of fractured needle ends inside their bodies are not infrequent. Surgery is usually required for removing fractured needle ends.

In order to reduce this drawback, so-called cannula needles made of Teflon are usually employed. Cannula needles are equipped with a mandrel made of steel that serves to open a passage in the skin for the cannula and is then removed from the needle. However, such needles are complex and therefore they are expensive to manufacture. In addition, introduction of cannula needles into the patient's skin usually causes more discomfort and pain. Cannula needles therefore are not an efficient solution to the aforesaid problem and they are tolerated by patients almost only in case of particularly prolonged infusions, for instance lasting 24 hours, typical of diabetic patients.

It is therefore a main object of the invention to provide a solution to the aforesaid problem that is capable of industrial applicability and is inexpensive and effective.

A further object of the invention is to provide a device for infusing a fluid substance into the body of a living being that is easy to use also for subjects that are movement-hindered, for instance owing to a disease.

A not least object of the invention is to provide a device of the aforementioned type that is safe for use and stable once implanted into the skin.

SUMMARY

These and other objects are achieved by the device for infusing a fluid substance into the body of a living being as claimed in the appended claims.

A main advantage of the device according to the invention derives from the extraordinary reduction of the risk of needle breaking in the bending zone as well as in other zones.

This result is obtained mainly by the fact that the device has a curved middle portion which confers a certain flexibility to the duct body defining the needle. This flexibility allows to absorb the energy generated by the forces applied to the device itself, when this is implanted into the skin of a living being. In this configuration of use, indeed, the distal portion is inserted into the skin without the possibility of moving. The forces applied to the remaining portion of the device, i.e. the portion that usually remains outside the patient's body, are absorbed by the middle portion. Thanks to the invention absorption of this energy by the 90° bent zone is therefore prevented.

According to an embodiment of the invention, the needle body is housed within a housing from which only the pointed end projects. In a first variant of this embodiment, the needle is incorporated in the housing body, which will preferably be made of a material capable of some deformation, in order to allow flexing of the needle flexible section. In another variant, the needle flexible section is free of flexing inside the housing, which therefore does not interfere with said flexible section.

BRIEF DESCRIPTION OF THE DRAWINGS

Some preferred embodiments of the invention will be given by way of non-limiting examples in the following description with reference to the annexed figures, in which.

DETAILED DESCRIPTION

Figure 1:
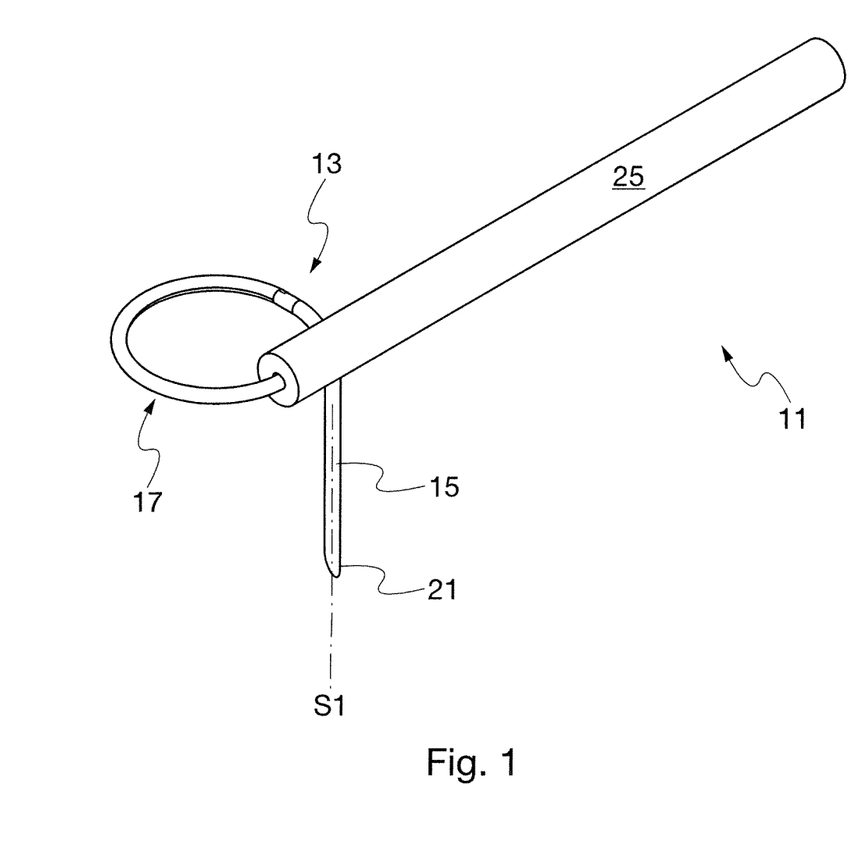
FIG. 1 is a perspective view of the device according to a first embodiment of the invention.
Figure 2:
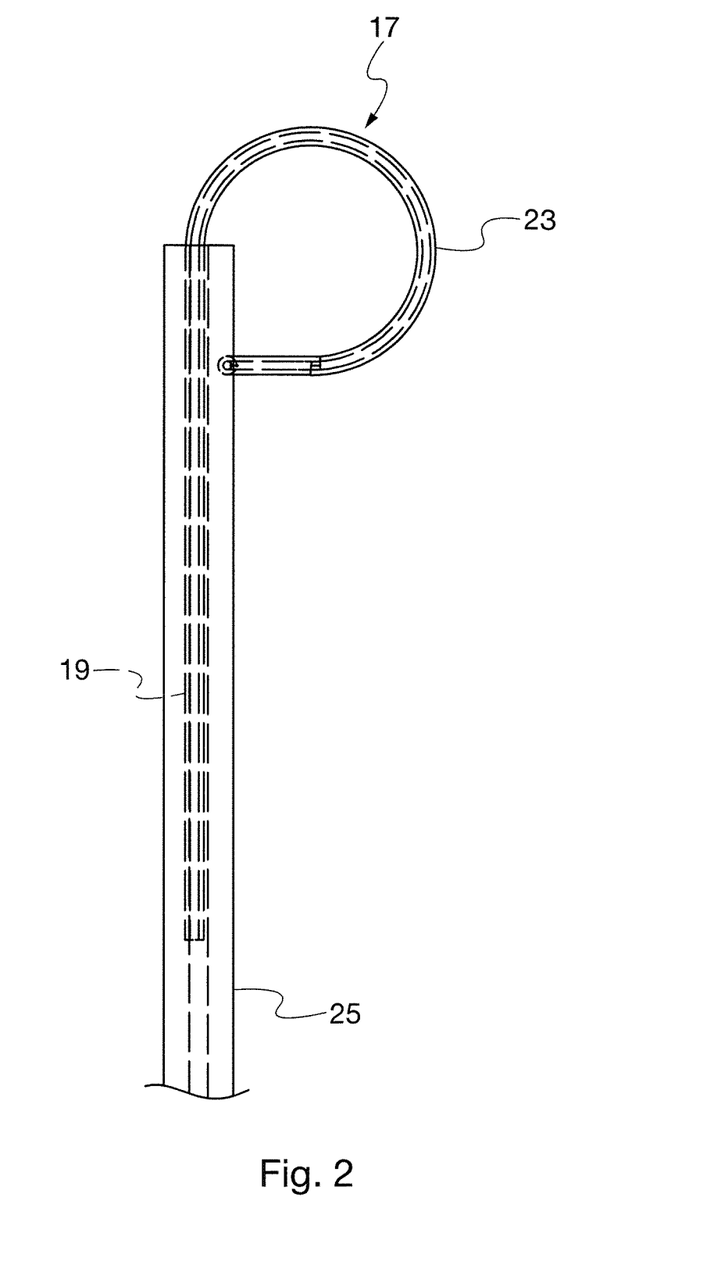
FIG. 2 is a top plan view, partially in section, of the device of FIG. 1.

With reference to FIGS. 1 and 2 there is illustrated a first embodiment of the invention. The device for infusing a fluid substance into the body of a living being according to the invention is identified as a whole with reference numeral 11. The device 11 comprises a hollow duct body 13 in which a distal portion 15, a middle portion 17 and a proximal portion 19 are defined. The distal portion 15 terminates with a pointed end 21 and extends along an axis S1. According to the invention the body 13 is preferably made of stainless steel.

According to the invention the middle portion 17 comprises a curved section 23 extending in a plane substantially perpendicular to the axis S1. Referring particularly to FIG. 2, the plane in which the section 23 extends is represented by the plane of the sheet and the axis S1 is perpendicular to the sheet.

Advantageously, according to the invention, the curved shape of the curved section 23 confers a certain flexibility to the section itself.

In particular, the flexibility obtained by providing the curved section 23 is capable of absorbing the energy that would by conveyed from the proximal portion 19 to the distal portion 15 and vice versa, when forces are applied to the device that tend to vary the spatial arrangement between the proximal portion 19 and the distal portion 15.

According to the invention the curved section 23 extends along an arc of circle of at least 120° in order to confer sufficient flexibility.

Still more preferably, the curved section 23 defines a corresponding ring and extends along an arc of circle comprised between about 270° and 360° in the plane perpendicular to the axis S1 of the distal portion 15. In this way the necessary flexibility is granted in all radial directions in the plane in which the intermediate portion 17 extends.

In addition, it is also possible to provide that the curved section 23 extends over a spiral path by making over a complete turn, for instance two or three turns.

The proximal portion 19 is also apt to receive the end part of a duct 25 for transporting fluid towards the distal portion 15. The duct 25 can for instance be made of a plastic material and can be flexible. The duct 25 is for example a typical cannula duct suitable for transporting an injectable drug in liquid form. The opposite end of the duct 25 relative to the end fitted on the proximal portion 19 is associated to a drug reservoir consisting for instance of an ampoule or syringe or the like. Furthermore, the drug reservoir can be associated to an electromechanical device such as a drug infusion pump.

In the embodiment shown in FIGS. 1 and 2, the curved section 23 defines a corresponding ring and therefore extends along an arc of circle of approximately 360° in the plane perpendicular to the axis S1 of the distal portion 15. Still with reference to the illustrated embodiment, the proximal portion 19 preferably lies in a plane parallel to the plane in which the middle portion 17 extends.

The proximal portion 19 and the distal portion 15 are preferably rectilinear, with their axes perpendicular to each other.

As it can be seen from FIG. 2, the proximal portion 19 extends over a length span that may vary depending on the applications in order to allow it to receive the duct 25 for the fluid.

The dimensions of the device 11 can be those typical of a needle for infusing drugs into the body of a living being, in particular of a human being. For example, the device 11 may have a distal end 15 having a length from 6 to 12 mm, a middle portion 17 with a diameter of the curved section comprised between 5 and 10 mm and a proximal end 19 having a length from 10 to 20 mm. The outer diameter of the cross-section of the hollow duct body 13 and of the corresponding passage for the fluid are chosen depending on the applications. Said diameters are for instance those common for a drug infusion needle for hypodermic use. The outer diameter is for example typically lower than 0.5 mm.

Referring to FIGS. from 3 to 5, there is illustrated a second embodiment of the invention, wherein the hollow duct body 13 is partially housed in a protective housing 27. In the embodiment shown, the housing 27 has a flat base 29 centrally provided with a cylindrical portion 31 which has an axis parallel to the axis S1 of the distal portion 15. The base 29 has a substantially circular shape. The cylindrical portion 31 further houses the middle portion 17 of the duct body 13. The distal portion 15 of the duct body 13 projects from the lower base of the cylindrical portion 31. The base 29 further comprises a second cylindrical portion 33 which is perpendicular to the axis of the cylindrical portion 31 and therefore parallel to the plane in which the middle portion 17 extends. The cylindrical portion 33 houses the proximal portion 19 of the duct body 13 and extends preferably over the entire diameter of the base 29. The first cylindrical portion 31 is further surrounded by a pair of halfmoon-shaped tabs 35. The tabs 35 are attached along their ends 37 to the base 29. The tabs 35 generally assume a configuration which is coplanar to the base 29. When necessary, the tabs 35 can however be pulled upwards towards each other so as to become perpendicular to the base 29, thus assuming the configuration shown in FIG. 6. The tabs 35 have the function of allowing, when pulled upwards, to easily grip the device 11 with the fingers.

Figure 3:
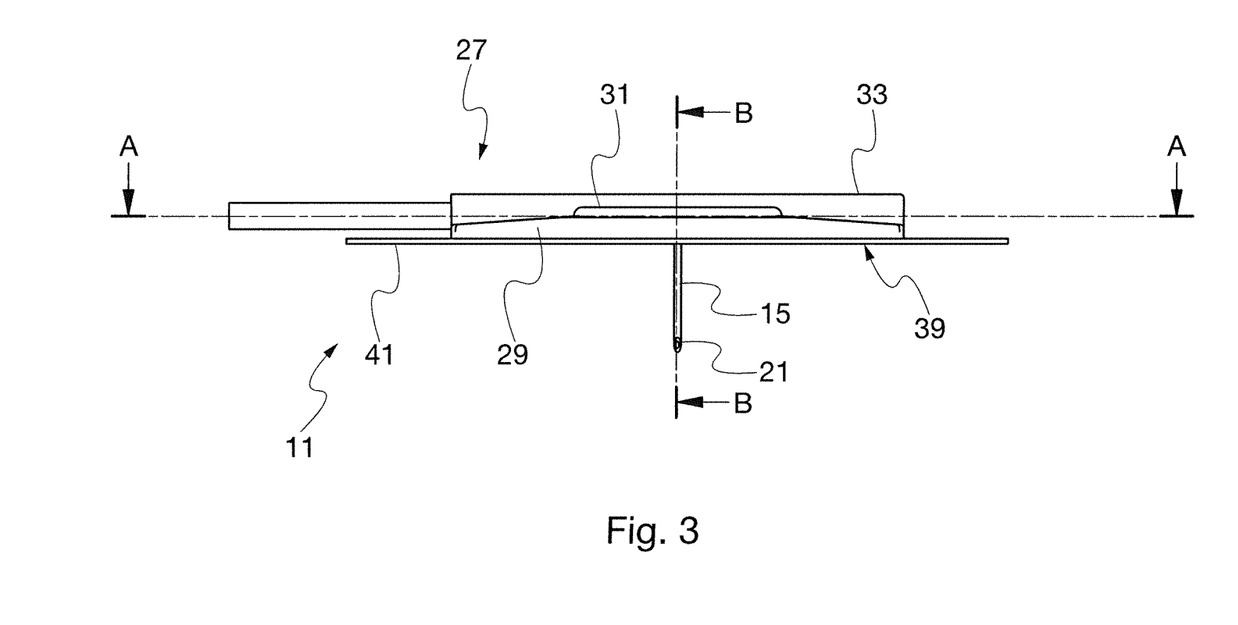
FIG. 3 is a side view of a second embodiment of the device.
Figure 4:
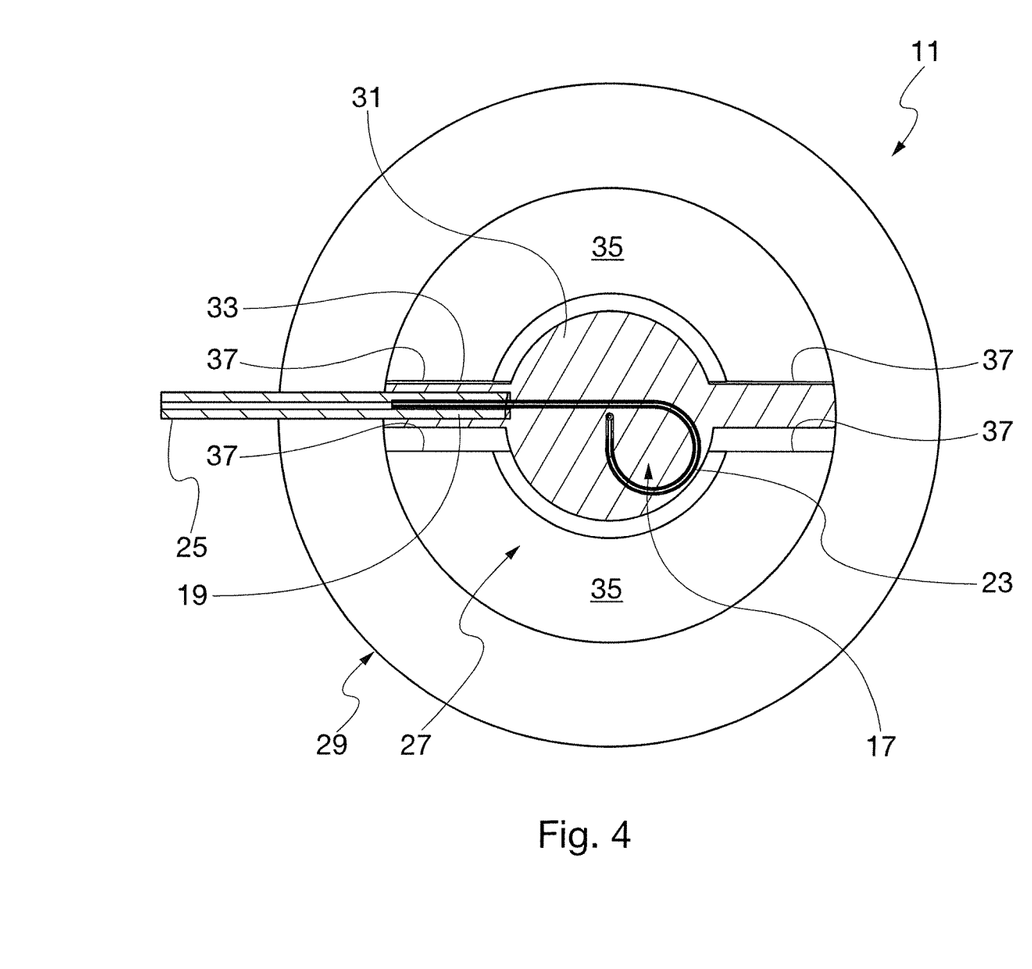
FIG. 4 is a sectional view of the device of FIG. 3 taken along the plane A-A of FIG. 3.
Figure 5:
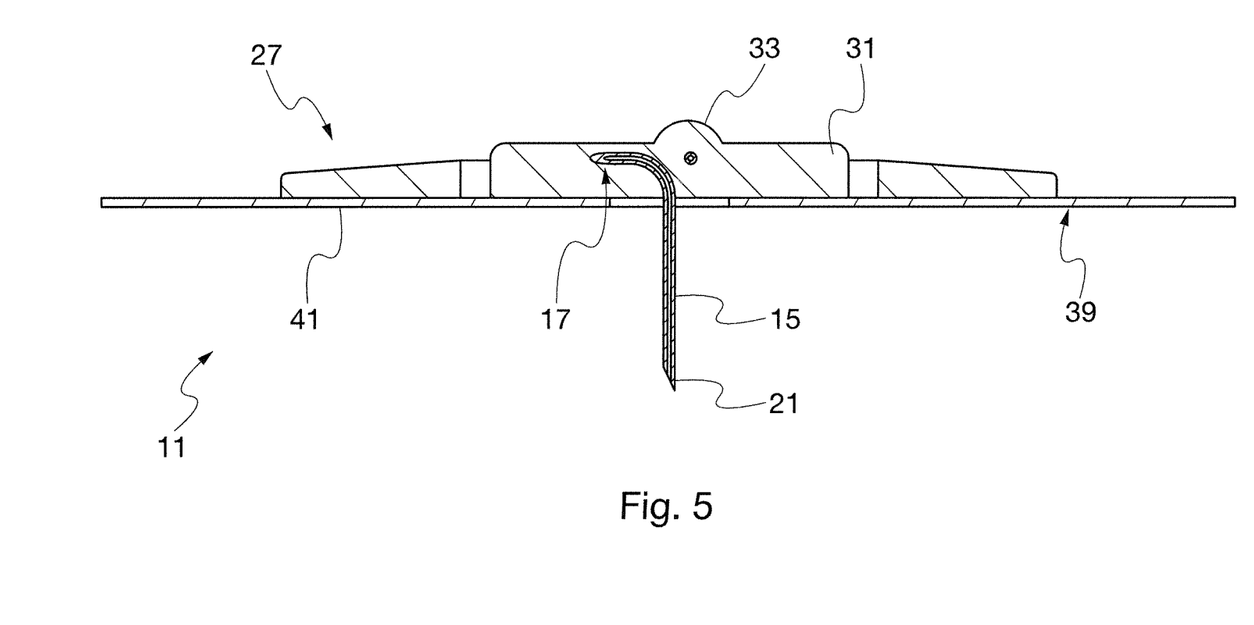
FIG. 5 is a sectional view of the device of FIG. 3 taken along the plane B-B of FIG. 3.
Figure 6:
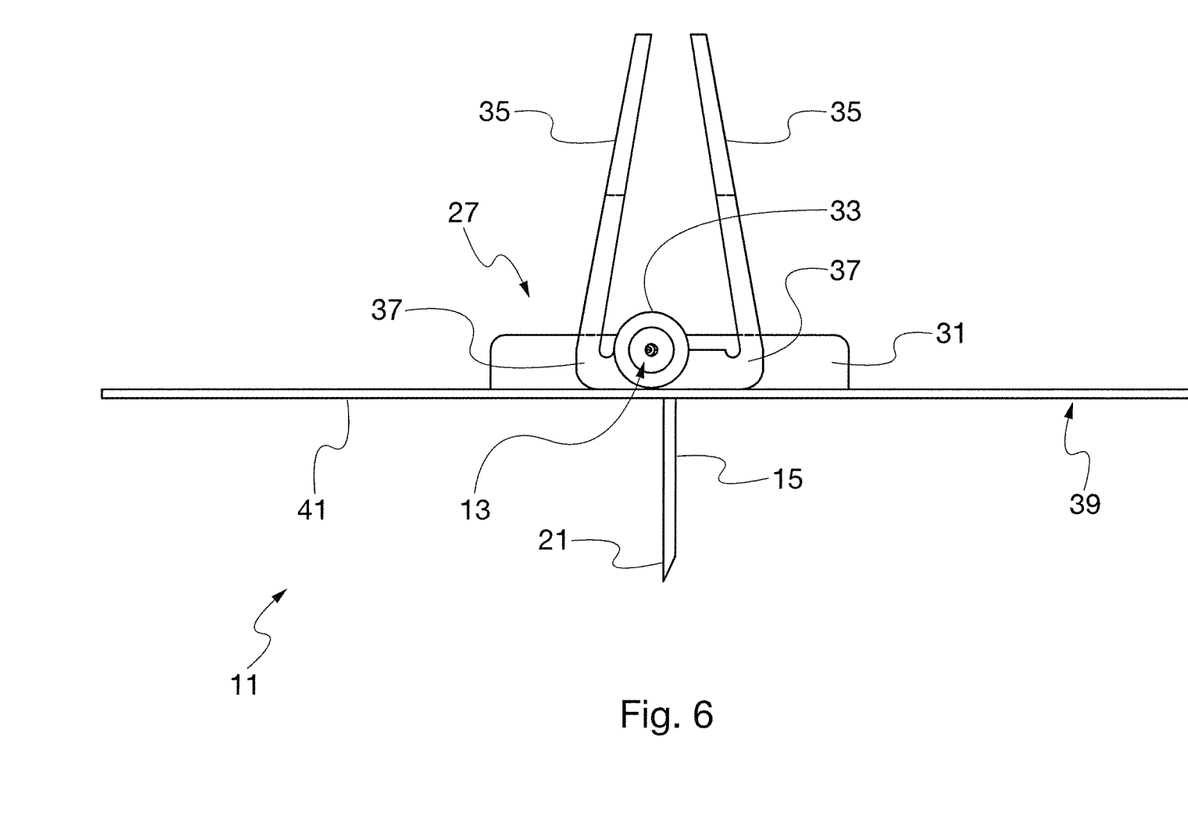
FIG. 6 is a side view of the device of FIG. 3, with tabs pulled upwards.

The base 29 has its surface opposite to the tabs 35, or lower surface 39, which is preferably adhesive. The adhesive surface 39 is further usually covered by a protective film 41 which can be removed when necessary. The film 41 may advantageously comprise a free edge (not shown) which projects from the surface 39 and facilitates gripping of the film 41 with the fingers.

In an embodiment the part of the duct body 13 housed in the housing 27 is incorporated in the material of which said housing is made. In this case the protective housing 27 is preferably made of rubber or similar material, which confers a certain liberty of movement for the curved section 23. The making can for instance be effected with the co-moulding technique.

In another embodiment the middle portion 17 of the duct body 13 is surrounded by the housing 27, without the material interfering with said portion 17, thus leaving the section 23 free to flex.

After the protective film 41 has been removed, thus leaving the adhesive surface 39 free, the device is ready for use. The distal portion 15 is introduced into the skin of a living being until the surface 39 adheres to the skin surrounding the hole into which the distal portion 15 is introduced. At this point the proximal portion 19 adheres to the skin and possible movements can be absorbed by the flexible section 23 housed in the housing 27.

The device as described and illustrated is capable of several variants and modifications falling within the same inventive principle.

The invention claimed is:

1. A device (11) for infusing a fluid substance into a body of a living being, comprising a hollow duct body (13) in which a distal portion (15), a middle portion (17) and a proximal portion (19) are defined, wherein the hollow duct body (13) is made entirely of stainless steel of a constant diameter and only includes a pair of openings located only at opposite terminating ends thereof at an end tip of the distal portion (15) and an end tip of the proximal portion (19) and is seamless without other openings therebetween, wherein the distal portion (15) terminates with a pointed end (21) and extends along an axis substantially perpendicular to a plane in which the middle portion (17) extends, wherein the middle portion (17) comprises a curved section (23) which extends along an arc of a circle for 270° to 360° about said circle in the plane perpendicular to the axis of the distal portion, wherein the distal portion, the middle portion, and the proximal portion of the hollow duct body do not extend within an interior of the circle; wherein the proximal portion (19) is a straight portion that is tangent to said circle along which said curved section (23) extends, wherein the hollow duct body is partially housed in a protective housing (27) made of rubber or a material similar to rubber, wherein the protective housing (27) has a flat base (29) centrally provided with a first cylindrical portion (31) which has an axis parallel to the axis of the distal portion (15) of the hollow duct body (13) and houses the middle portion (17) of the hollow duct body (13) and from which the distal portion (15) of the hollow duct body (13) projects, wherein the flat base (29) further comprises a second cylindrical portion (33) which is perpendicular to the axis of the first cylindrical portion (31) of the protective housing (27) and houses the proximal portion (19) of the hollow duct body (13) such that the end tip of the proximal portion (19) is accessible for receiving an end part of a duct (25) for transporting fluid towards the distal portion (15) of the hollow duct body (13), wherein the entire middle portion (17) of the hollow duct body (13) housed in the protective housing (27) is embedded within the rubber or material similar to rubber of which said protective housing is made and which confers a certain liberty of movement for the curved section (23) of the middle portion (17) of the hollow duct body (13), and wherein the curved section (23) confers a certain flexibility to the curved section itself, capable of absorbing an energy that would be conveyed from the proximal portion (19) of the hollow duct body (13) to the distal portion (15) of the hollow duct body (13) and vice versa, when forces are applied to the device that tend to vary a spatial arrangement between the proximal portion (19) of the hollow duct body (13) and the distal portion (15) of the hollow duct body (13).

2. The device according to claim 1, wherein the distal portion (15) and the proximal portion (19) extend along corresponding perpendicular axes and wherein the proximal portion (19) lies in a plane parallel to the plane on which the curved section (23) extends.

3. A device (11) for infusing a fluid substance into a body of a living being, comprising:

a hollow duct body (13) in which a distal portion (15), a middle portion (17) and a proximal portion (19) are defined such that the distal portion (15) terminates with a pointed end (21) and extends along an axis substantially perpendicular to a plane in which the middle portion (17) extends, the middle portion (17) comprises a curved section (23) which extends along an arc of a circle for 270° to 360° about said circle in the plane perpendicular to the axis of the distal portion such that the distal portion, the middle portion, and the proximal portion of the hollow duct body do not extend within an interior of the circle, the proximal portion (19) is a straight portion that is tangent to said circle along which said curved section (23) extends, and the hollow duct body (13) is made entirely of stainless steel of a constant diameter and only includes a pair of openings located only at opposite terminating ends thereof at an end tip of the distal portion (15) and an end tip of the proximal portion (19) and is seamless without other openings therebetween; and a protective housing (27) made of rubber in which the hollow duct body (13) is at least partially housed, the protective housing (27) having a flat base (29) centrally provided with a first cylindrical portion (31) which has an axis parallel to the axis of the distal portion (15) of the hollow duct body (13) and houses the middle portion (17) of the hollow duct body (13) and from which the distal portion (15) of the hollow duct body (13) projects;

wherein the flat base (29) further comprises a second cylindrical portion (33) which is perpendicular to the axis of the first cylindrical portion (31) of the protective housing (27) and houses the proximal portion (19) of the hollow duct body (13) such that the end tip of the proximal portion (19) is accessible for receiving an end part of a duct (25) for transporting fluid towards the distal portion (15) of the hollow duct body (13);

wherein the middle portion (17) of the hollow duct body (13) housed in the protective housing (27) is entirely embedded within the rubber of which said protective housing is made and which confers a certain liberty of movement for the curved section (23) of the middle portion (17) of the hollow duct body (13);

wherein the curved section (23) confers a certain flexibility to the curved section itself, capable of absorbing an energy that would be conveyed from the proximal portion (19) of the hollow duct body (13) to the distal portion (15) of the hollow duct body (13) and vice versa, when forces are applied to the device that tend to vary a spatial arrangement between the proximal portion (19) of the hollow duct body (13) and the distal portion (15) of the hollow duct body (13); and wherein the first cylindrical portion (31) is surrounded by a pair of halfmoon-shaped tabs (35) attached along their ends (37) to the base (29) of the housing (27), said tabs being capable of assuming a configuration coplanar with the base (29) of the housing (27) and a configuration perpendicular to the base (29) of the housing (27).

* * * * *